United States Patent [19]

Summerville, deceased et al.

[11] 4,440,946

[45] Apr. 3, 1984

[54] PRODUCTION OF ESTERS FROM ALDEHYDES USING A SILVER/CADMIUM/ZINC/ZIRCONIUM CATALYST

[75] Inventors: Richard H. Summerville, deceased, late of W. Orange, N.J.; James E. Summerville, Jr., administrator, Signal Mountain, Tenn.

[73] Assignee: Celanese Corporation, New York, N.Y.

[21] Appl. No.: 401,607

[22] Filed: Jul. 26, 1982

[51] Int. Cl.$^3$ .......................... C07C 67/24; B01J 23/06
[52] U.S. Cl. .................................... 560/210; 502/343; 560/64; 560/96; 560/103; 560/105; 560/190; 560/226; 560/238; 546/319; 546/327
[58] Field of Search ................... 560/210, 238, 64, 96, 560/103, 105, 190, 226; 502/343; 546/319, 327

[56] References Cited

U.S. PATENT DOCUMENTS 4,052,424  10/1977  Vanderspurt .................... 560/240

OTHER PUBLICATIONS

Frolich et al., *Chemical Abstracts,* vol. 24, (1930), p. 2660$^7$.
Kirk-Othmer, *Encyclopedia of Chemical Technology,* 2nd Ed., vol. 22, p. 616.

*Primary Examiner*—Natalie Trousof
*Assistant Examiner*—L. Hendriksen
*Attorney, Agent, or Firm*—Depaoli & O'Brien

[57] ABSTRACT

This invention is a process for producing a carboxylate ester which involves contacting mixtures of alcohol and aldehyde in vapor phase with a reduced silver-cadmium-zinc-zirconium catalyst composition.

15 Claims, No Drawings

PRODUCTION OF ESTERS FROM ALDEHYDES USING A SILVER/CADMIUM/ZINC/ZIRCONIUM CATALYST

BACKGROUND OF THE INVENTION

Carboxylate esters are produced by a range of procedures which involve reaction mechanisms such as oxidation, disproportionation or dehydrogenation, as directed to reactants such as alcohols, aldehydes, acetals, and the like.

The Tishchenko reaction is illustrative of an early prior art method of ester synthesis. The process involves disproportionation of an aldehyde such as acetaldehyde into the corresponding ester, e.g., ethyl acetate, in the presence of an aluminum alkoxide catalyst.

U.S. Pat. No. 1,869,761 discloses a process for vapor phase conversion of alcohols to esters in the presence of a silver-uranium carbonate catalyst.

U.S. Pat. No. 1,975,853 describes a process for producing ethyl acetate by contacting ethanol in vapor phase under high pressure with a catalyst consisting of metallic copper and a difficultly reducible oxide.

U.S. Pat. No. 2,012,993 proposes the inclusion of water in a reaction mixture of an alcohol and a dehydrogenation catalyst to suppress the formation of higher alcohols and increase the production of ester derivatives.

U.S. Pat. No. 2,504,497 discloses a new type of catalyst for dehydrogenation of alcohols to esters. The catalyst consists of a porous aluminum-copper alloy composition.

U.S. Pat. No. 3,188,330 discloses a liquid phase method for converting alcohols into ketones and esters in the presence of a carboxylic acid salt of a Group IIB metal, e.g., cadmium or zinc.

U.S. Pat. No. 3,287,401 describes the production of esters by the reaction of an alcohol/aldehyde mixture at 200°–600° F. in the presence of a molybdenum-containing catalyst such as sulfided cobalt molybdate.

U.S. Pat. No. 3,452,067 proposes the use of a supported molybdenum sulfide catalyst for dehydrogenation of alcohols to esters in the vapor phase.

U.S. Pat. No. 3,639,449 discloses a process for converting alcohols to esters by reaction with molecular oxygen in the presence of a palladium or rhodium oxide catalyst.

U.S. Pat. No. 3,819,685 describes the preparation of acrylic esters and methacrylic esters by reaction of acrolein or methacrolein with an alcohol and molecular oxygen in the presence of a cobalt-molybdenum type of oxidation catalyst.

U.S. Pat. No. 4,052,424 discloses a process for producing alkyl alkanoate esters which involves contacting a primary alkanol in vapor phase with a silver-cadmium alloy or silver-cadmium-zinc alloy catalyst at 250°–600° C.

There has been a continuing research effort to develop improved catalysts and procedures to overcome the disadvantages of known processes for converting alcohols and/or aldehydes to carboxylate esters. A main disadvantage is the low conversion selectivity to the desired products, and the concomitant formation of major proportions of byproducts such as carbon dioxide and aldol condensates.

Accordingly, it is an object of this invention to provide a one-step vapor phase process for converting an alcohol/aldehyde mixture into carboxylate ester product with high conversion and selectivity. For example, wherein the conversion of aliphatic aldehyde is at least about 90 percent, and the selectivity to ester product is at least about 70 percent based on the aliphatic aldehyde.

It is another object of this invention to provide a novel dehydrogenation catalyst composition which exhibits high selectivity for the conversion of an alcohol/aldehyde mixture via a hemiacetal intermediate to carboxylate ester product.

Other objects and advantages of the present invention shall become apparent from the following description and examples.

DESCRIPTION OF THE INVENTION

One or more objects of the present invention are accomplished by the provision of a process for producing a carboxylate ester which comprises contacting a mixture of alcohol and aldehyde in vapor phase with a reduced catalyst composition comprising silver-cadmium-zinc-zirconium which is at least partially in the free metal form.

In one of its embodiments, the present invention provides a process for producing a carboxylate ester which comprises contacting a mixture of aliphatic alcohol and aliphatic aldehyde with a metal catalyst composition comprising $$Ag_{1.0}Cd_{0.1-1.5}Zn_{0.1-1}Zr_{0.5-2.0}K_{0-0.6}$$

at a temperature between about 225°–325° C.

The conversion of alcohol/aldehyde to carboxylate ester proceeds rapidly and with high selectivity, presumably via a hemiacetal intermediate:

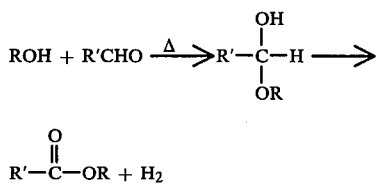

The R and R' substituents represent organic radicals such as $C_1$–$C_8$ aliphatic groups.

The dehydrogenation of hemiacetals to esters is essentially thermoneutral. In contrast, the dehydrogenation of an alcohol such as ethanol to acetaldehyde is endothermic by 16 Kcal/mole.

The invention process is amenable to alcohols and aldehydes which have appropriate volatility and stability and reactivity under the vapor phase catalytic conditions of the process.

The alcohol reactant can be selected from primary, secondary and tertiary carbinols which can be saturated or unsaturated, straight chain or branched, cyclic or acyclic, aliphatic or aromatic, monohydric or polyhydric, and can contain heteroatoms which do not interfere with the reactivity of the hydroxyl moiety in the alcohols.

Illustrative of alcohol reactants are methanol, ethanol, propanol, butanol, pentanol, hexanol, heptanol, octanol, dodecanol, tetradecanol, hexadecanol, octadecanol, allyl alcohol, crotyl alcohol, β-methallyl alcohol, octenol, dodecenol, cyclohexanol, phenol, cresol, benzyl alcohol, ethyleneglycol, propyleneglycol, hydroquinone, p-hydroxybenzyl alcohol, and the like.

A preferred type of alcohol reactant is a primary $C_1$–$C_8$ alkanol or $C_1$–$C_8$ alkenol which has the stability and reactivity to yield optimal results under vapor phase process conditions.

The aldehyde reactant employed in the process can be selected from aliphatic and aromatic compounds as illustrated by formaldehyde, acetaldehyde, propionaldehyde, butyraldehyde, glyoxal, ethylene dialdehyde, acrolein, methacrolein, crotonaldehyde, acetylene dialdehyde, benzaldehyde, tolualdehyde, benzylaldehyde, phthaldialdehyde, terephthaldialdehyde, and the like, and heteroatom-containing compounds such as chloroacetaldehyde, p-methoxybenzaldehyde and pyridinealdehyde.

A preferred type of aldehyde reactant is an aliphatic aldehyde such as $C_1$–$C_8$ alkanal or $C_1$–$C_8$ alkenal.

The alcohol and aldehyde reactants are employed in admixture containing between about 0.5:1 to 5:1 reactive equivalents of alcohol per reactive equivalent of aldehyde.

In the practice of the invention process, preferably the alcohol/aldehyde admixture is vaporized and passed through a reaction zone containing the invention dehydrogenation catalyst composition. The catalyst can be in the form of a fixed, moving or fluidized bed. A continuous mode of operation is preferred.

The alcohol/aldehyde feed stream can contain a gasiform diluent such as nitrogen, carbon monoxide, methane, carbon dioxide, helium, hydrogen, and the like. The diluent can be employed in quantity which can vary broadly over the range between about 0.1–100 moles per mole of alcohol/aldehyde reactants.

The presence of a minor quantity of molecular oxygen can be tolerated without deleterious effect. Any molecular oxygen in the reaction zone combines with hydrogen to form water in a highly exothermic reaction:

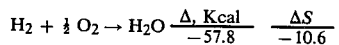

It is preferred that any molecular oxygen present should not exceed more than about 0.1 mole per mole of alcohol/aldehyde reactants in the dehydrogenation reaction zone.

The reaction zone temperature can vary in the range between about 200°–400° C., and the preferred range is between about 225°–325° C. The contact time between reactants and catalyst will vary in the range between about 1–20 seconds.

The pressure in the reaction system is not a critical factor, and the process can be conducted at a pressure between about 10–1000 psi, and normally the system will be operated conveniently at ambient pressure.

An important aspect of the present invention is the provision of a novel silver(1.0)-cadmium(0.1–1.5)-Zn(0.1–1)-zirconium(0.5–2.0)-potassium(0–0.6) catalyst composition which is substantially in the free metal form (i.e., metals of zero valence). The said catalyst composition has exceptional dehydrogenation activity for the selective conversion of alcohol/aldehyde to carboxylate ester in accordance with the invention process. A preferred catalyst composition is one containing between about 0.1–0.6 atomic weight of potassium per atomic weight of silver. The presence of potassium appears to enhance the stability and reactivity of the catalyst composition.

Each of the silver, cadmium, zinc and zirconium metals is an essential component of the catalyst composition in order to achieve optimal conversion and selectivity to the desired carboxylate ester product in the process. For example, if zirconium metal is omitted from the catalyst composition there is a precipitous loss of conversion selectivity of alcohol/aldehyde to carboxylate ester. The absence of any of silver, cadmium or zinc components also results in loss of catalytic selectivity to carboxylate ester, and an increase of hydrogen transfer activity, aldol condensation activity, and the like, which lead to byproduct formation.

As illustrated in Example I, the catalyst compositions can be prepared by coprecipitating hydroxides of silver, cadmium, zinc and zirconium from an aqueous medium containing calculated quantities of water-soluble salts of the said metal elements. The precipitation is effected by the addition of caustic to the aqueous solution. If potassium is to be a component of the catalyst composition, the caustic can be added to the precipitation medium in the form of potassium hydroxide. A quantity of potassium compound becomes incorporated in the coprecipitate which separates from the alkaline aqueous medium.

If a carrier substrate is to be included in the catalyst composition, the selected material in powder form can be slurried in the aqueous medium prior to or after the precipitation of the water-soluble metal salts. Suitable carrier substrates include silica, alumina, silica-alumina, kieselguhr, titanium oxide, pumice, carborundum, boria, and the like. The quantity of carrier substrate in the catalyst composition can vary in the range between about 5–99.5 percent, based on the total catalyst weight.

After the coprecipitation phase is completed, the coprecipitate is recovered by filtration or other conventional means. This step is followed by water-washing of the solids, drying, and a subsequent treatment with a reducing gas such as hydrogen to convert the metal compounds in the catalyst composition substantially into the active free metal form. Alternatively, the metal compounds in the catalyst precursor can be reduced in the initial stage of a process such as the present invention dehydrogenation reaction in which a reducing gas such as hydrogen is generated.

The following examples are further illustrative of the present invention. The reactants and catalysts and other specific ingredients are presented as being typical, and various modifications can be derived in view of the foregoing disclosure within the scope of the invention.

EXAMPLE I

This Example illustrates the preparation of catalyst compositions useful for application in the present invention process for carboxylate ester production.

(A)

A solution (1) is prepared by dissolving $ZrO(NO_3)_2 \cdot XH_2O$ (25 g, 0.1 mole), $AgNO_3$ (17 g, 0.1 mole), $Zn(NO_3)_2 \cdot 6H_2O$ (29.7 g, 0.1 mole) and $Cd(NO_3)_2 \cdot 4H_2O$ (30.9 g, 0.1 mole) in 180 ml of doubly distilled water. A second solution (2) is prepared by dissolving 453.5 g of 85% analytical reagent KOH in 1500 ml of doubly distilled water. The two solutions are simultaneously added from separate addition funnels to 300 ml of rapidly stirred water in a 3 liter beaker. The addition of solution (2) is controlled to maintain a constant pH of 12 during the addition (precipitation). The addition of solution (2) is stopped when all of solution (1) has been added.

The mixture is stirred for one hour, then the precipitate is collected on a fritted filter and washed twice with 500 ml portions of doubly distilled water. The solid is dried under suction for one hour, then placed in a forced draft oven at 110° C. for one hour.

The solid is reduced at 1 atm. and 200° C. in flowing hydrogen for seven hours. Chemical analysis indicates a content of 22.5% Ag, 24.6% Cd, 17.4% Zr, 12.2% Zn and 0.14% K.

(B)

A catalyst is prepared as in section A above except that the precipitation pH is maintained at 13. The composition has a content of 25.5% Ag, 26.5% Cd, 22.2% Zr, 13.1% Zn and 0.08% K.

(C)

A catalyst is prepared as in Section A except that the precipitation pH is maintained at 14. The composition content is 27.5% Ag, 29.3% Cd, 23.5% Zr, 3.3% Zn and 1.1% K.

(D)

Two solutions are prepared by dissolving $AgNO_3$ (33.97 g, 0.2 mole), $Cd(NO_3)_2.4H_2O$ (47.3 g, 0.15 mole), $Zn(NO_3)_2.6H_2O$ (37.9 g, 0.13 mole) and $ZrO(NO_3)_2.XH_2O$ (49.2 g, 0.2 mole) in 350 ml $H_2O$, and 91.24 g KOH (85%) in 350 ml $H_2O$. These two solutions are poured simultaneously into 500 ml of rapidly stirred water in a 2 liter beaker. The mixture is stirred for one hour then filtered. The solid is washed three times with doubly distilled water then left in the dark overnight. The solid is dried at 125° C. in a combustion tube under $N_2$, then reduced in flowing $H_2$ at 200° C. (1 atm.).

If an internal diluent is to be employed, e.g., a silica carrier, then the solutions described above are added to a slurry of a carrier substrate powder during the catalyst preparation.

The potassium-containing reagent is eliminated when a potassium-free AgCdZnZr catalyst composition is desired. In this case, the pH of the catalyst preparation medium is controlled with a reagent other than potassium hydroxide, e.g., ammonium hydroxide, or an hydroxide of one of the other metal elements being incorporated in the catalyst composition.

EXAMPLE II

This Example illustrates the vapor phase production of ethyl propionate in accordance with the present invention process.

The reactor is a 316SS tube of 1 cm diameter and 20 cm long. It is heated in a Lindberg furnace fitted with an electrically insulated copper liner to provide an isothermal zone. The liquid feed streams are evaporated in two flashers located in an oven held at 120° C. The flashers are fed from ISCO syringe pumps. Small flows of $N_2$ (20 ml/min) are used to carry the vapors from the flashers to a mixer. After the mixer, a sample can be taken by a microvolume gas sampling valve for GC analysis. (Pentane added to the reactants serves as an internal standard.)

The vapor phase reaction mixture is passed through the reactor, then through another gas sampling valve and collected in a stainless steel jacketed condenser cooled to dry ice temperature. The internal temperature is −38° C. to −42° C. "Dry" gases and some pentane passing through the condenser are analyzed. Mass accountabilities in this system are 85–115% using the pentane internal standard.

Analysis of products is performed by GC methods appropriate to the reaction mixture and starting products.

A series of runs is conducted by passing various vapor mixtures of ethanol/propionaldehyde through the above-described reactor containing one of AgCdZnZrK, AgCdZnZrK/$SiO_2$, AgCdZnZr, AgCdZnK/$SiO_2$, AgCdZnK, AgZnZrK, AgCdZn/$SiO_2$, AgZnZrK and ZnO catalyst compositions, under various combinations of reaction conditions.

Superior results are obtained with the catalysts which contain AgCdZnZr and AgCdZnZrK metal constituents.

Employing an $Ag_{1.0}Cd_{0.76}Zn_{0.64}Zr_{0.81}$ catalyst, a reactor temperature of 250° C. and ambient pressure, a contact time of 9.1 seconds, and feed rates of ethanol (5.2 g/hr) and propionaldehyde (2.8 g/hr) in a seven day continuous run, the conversions of ethanol and propionaldehyde are 48 and 87.3 percent, respectively, the selectivity of ethanol to ethyl propionate is 83.7 percent, the selectivity of propionaldehyde to ethyl propionate is 69.1 percent, and the ethyl propionate Space-Time-Yield (STY) is 100–200 gram/liter hour.

Byproducts of the reaction include propanol, propyl propionate and 2-methyl-2-pentenal.

Excellent conversion and selectivity results are also obtained with an $Ag_{1.0}Cd_{0.9}Zn_{0.7}Zr_{1.0}K_{0.2}$ catalyst composition.

An AgCdZn/$SiO_2$ type catalyst as disclosed in U.S. Pat. No. 4,052,424 yields about 20 percent selectivity of propionaldehyde to ethyl propionate.

EXAMPLE III

This Example illustrates the production of methyl isobutyrate in accordance with the present invention process.

Employing the apparatus and procedures of Example II, a series of runs are conducted with a vapor mixture of methanol/isobutyraldehyde over various catalysts under different reaction conditions.

Excellent results are obtained with an $Ag_{1.0}Cd_{0.97}Zn_{0.79}Zr_{0.9}K_{0.024}$ catalyst which during preparation is precipitated from a slurry mixture maintained at a pH of 13–14.

Employing this catalyst, a reactor temperature of 270° C. and ambient pressure, a contact time of 4.4 seconds, and feed rates of methanol (5.28 g/hr) and isobutyraldehyde (3.95 g/hr), the conversions of methanol and isobutyraldehyde are 32.6 and 96.6 percent, respectively, the selectivity of methanol to methyl isobutyrate is 66.7 percent, the selectivity of isobutyraldehyde to methyl isobutyrate is 88.3 percent, and the methyl isobutyrate STY is 477 gram/liter hours.

Variations in temperature and/or pressure do not change the reaction results to any appreciable degree.

EXAMPLE IV

This Example illustrates the production of methyl methacrylate and methallyl methacrylate in accordance with the present invention process.

The apparatus and procedure described in Example II are employed, the catalyst is $Ag_{1.0}Cd_{0.1}Zn_{0.1}Zr_{1.3}$, and the vapor phase feed stream is a mixture of methanol/methacrolein.

The reaction is conducted with a reactor temperature of 285° C. and a pressure of 0.5 psig, a contact time of about one second, and feed rates of methanol (3.2 g/hr), pentane (1.0 g/hr) and methacrolein (4.1 g/hr). The conversions of methanol and methacrolein are 0.6 and 16 percent, respectively, the selectivity of methanol to methyl methacrylate is 29 percent and the selectivities of methacrolein to methyl methacrylate and methallyl methacrylate are 13 and 22 percent, respectively.

EXAMPLE V

This Example illustrates the production of methyl heptanoate in accordance with the present invention process.

The catalyst is $Ag_{1.0}Cd_{1.0}Zn_{0.24}Zr_{0.93}K_{0.15}$, the vapor phase feed stream is a mixture of methanol/heptaldehyde, and the reaction is conducted continuously for 200 hours.

The reactor temperature is 250° C. and the pressure is 15 psig. The feed rates are methanol (4.4 g/hr) and heptaldehyde (2.2 g/hr). The conversions of methanol and heptaldehyde are 5.2 and 93.4 percent, respectively. The selectivity of heptaldehyde to methyl heptanoate is 90.4 percent. The selectivity of heptaldehyde to heptanol is 6.7 percent.

What is claimed is:

1. A process for producing a carboxylate ester which comprises contacting a mixture of alcohol and aldehyde in vapor phase with a coprecipitate catalyst composition comprising silver-cadmium-zinc-zirconium which is substantially in the free metal form.

2. A process for producing a carboxylate ester which comprises contacting a mixture of aliphatic alcohol and aliphatic aldehyde with a coprecipitate catalyst composition comprising $Ag_{1.0}Cd_{0.1-1.5}Zn_{0.1-1}Zr_{0.5-2.0}K_{0-0.6}$ which is substantially in the free metal form, at a temperature between about 225°-325° C.

3. A process in accordance with claim 2 wherein the aliphatic alcohol reactant is a primary $C_1-C_8$ alkanol or $C_1-C_8$ alkenal.

4. A process in accordance with claim 2 wherein the aliphatic aldehyde is a $C_1-C_8$ alkanal or $C_1-C_8$ alkenal.

5. A process in accordance with claim 2 wherein the catalyst composition has a $K_{0.01-6}$ metal content.

6. A process in accordance with claim 2 wherein the alkanol and aliphatic aldehyde reactants are in a molar ratio between about 0.5:1 and 5:1 of alkanol/aldehyde.

7. A process in accordance with claim 2 wherein the reaction is conducted in vapor phase employing an inert diluent component.

8. A process in accordance with claim 2 wherein the contact time of the alkanol and aliphatic aldehyde reactants with the catalyst composition is between about 1-20 seconds.

9. A process in accordance with claim 2 wherein the reactants are ethanol and propionaldehyde, and the recovered ester product is ethyl propionate.

10. A process in accordance with claim 2 wherein the reactants are methanol and isobutyraldehyde, and the recovered ester product is methyl isobutyrate.

11. A process in accordance with claim 2 wherein the reactants are methanol and methacrolein and the recovered ester product is a mixture of methyl methacrylate and methallyl methacrylate.

12. A process in accordance with claim 2 wherein the reactants are methanol and heptaldehyde, and the recovered ester product is methyl heptanoate.

13. A process in accordance with claim 2 wherein the reactants are allyl alcohol and acetaldehyde, and the recovered ester product is allyl acetate.

14. A process in accordance with claim 2 wherein the conversion of aliphatic aldehyde is at least about 90 percent, and the selectivity to ester product is at least about 70 percent based on the aliphatic aldehyde.

15. A coprecipitate catalyst composition comprising $Ag_{1.0}Cd_{0.1-1.5}Zn_{0.1-1}Zr_{0.5-2.0}K_{0-0.6}$ which is substantially in the free metal form.

* * * * *